(12) United States Patent
Davanathan

(10) Patent No.: US 6,203,317 B1
(45) Date of Patent: Mar. 20, 2001

(54) ORTHODONTIC ELASTOMERIC LIGATURE WITH SLIPPERY COATING AND METHOD OF MAKING SAME

(75) Inventor: Thrumal Davanathan, Warsaw, IN (US)

(73) Assignee: TP Orthodontics, Inc., Westville, IN (US)

( * ) Notice: Subject to any disclaimer, the term of this patent is extended or adjusted under 35 U.S.C. 154(b) by 0 days.

(21) Appl. No.: 09/619,207

(22) Filed: Jul. 19, 2000

(51) Int. Cl.$^7$ .......................................................... A61C 3/00
(52) U.S. Cl. ................................................. 433/13; 433/22
(58) Field of Search ............................................ 433/8–24

(56) References Cited

U.S. PATENT DOCUMENTS

| | | |
|---|---|---|
| 3,530,583 | 9/1970 | Klein et al. . |
| 3,758,947 | 9/1973 | Kesling . |
| 4,100,309 | 7/1978 | Micklus et al. . |
| 4,642,267 | 2/1987 | Creasy et al. . |
| 4,900,250 | 2/1990 | Kesling et al. . |
| 5,378,146 | 1/1995 | Sterrett . |
| 5,419,913 * | 5/1995 | Podell et al. .......................... 424/448 |

* cited by examiner

Primary Examiner—Nicholas D. Lucchesi
(74) Attorney, Agent, or Firm—Lloyd L. Zickert

(57) ABSTRACT

An orthodontic elastomeric appliance with a polymer coating that becomes slippery when wetted, and a method of making the appliance which comprises the steps of forming an appliance of elastomeric material and coating the appliance with a polymer film capable of making the appliance slippery when wetted.

19 Claims, No Drawings

ORTHODONTIC ELASTOMERIC LIGATURE WITH SLIPPERY COATING AND METHOD OF MAKING SAME

DESCRIPTION

This invention relates in general to an orthodontic elastomeric appliance having a slippery outer surface when wetted and a method of making the appliance, wherein the appliance is formed of elastomeric material and coated with a polymer film which when wetted becomes slippery, and more particularly to an orthodontic polyurethane ligature having a slippery outer surface when wetted, and a method of making the ligature including molding the ligature of polyurethane and coating the ligature with a hydrophillic polymer blend so that the ligature, when used in the mouth and wetted, will have a slippery surface to facilitate the movement of brackets on an archwire and decrease treatment time.

BACKGROUND OF THE INVENTION

Heretofore, it has been well known to form orthodontic appliances of elastomeric material and to mold orthodontic ligatures of elastic urethane, such as shown in U.S. Pat. No. 3,530,583. Similarly, U.S. Pat. Nos. 3,758,947 and 4,900,250 also disclose the molding of orthodontic elastomeric appliances.

It has also been known to coat elastomeric medical devices with a hydrophillic film as shown in U.S. Pat. Nos. 4,100,309 and 4,642,267 so that the medical appliances when wet have a low coefficient of friction and are hydrophillic.

Orthodontic treatment of patients nearly always involves the use of metal, ceramic or plastic brackets in combination with metal archwires. The brackets are provided with archwire slots and tie wings for receiving ligatures to retain the archwires on the brackets. Generally, these ligatures are made of elastomeric material, including polyurethane, as above mentioned. Polyurethane ligatures exhibit a high contact adhesiveness to metal archwires. This contact adhesiveness creates an opposing force and inhibits the movement of brackets along an archwire, thereby increasing treatment time. This problem created by the ligatures has been addressed in the design of self-ligating brackets and other specialty brackets. However, such specialty brackets produce other problems such as loss of rotational control and the inability to use ligatures for cosmetic purposes.

SUMMARY OF THE INVENTION

The present invention solves the problem of contact adhesiveness by coating elastomeric ligatures with a polymer that exhibits slipperiness as soon as it is contacted by water or saliva in the mouth. Thus, the coated elastomeric ligatures of the present invention are slippery when wet and therefore overcome the contact adhesiveness problem to allow ease of movement of brackets along an archwire, thereby decreasing treatment time.

The present invention accordingly is in an orthodontic elastomeric appliance such as of polyurethane or other urethane material that is elastomeric and which is coated so that it will be slippery on the outer surface when wetted in the mouth. Any suitable polymer coating that becomes slippery when hydrated may be applied to the elastomeric appliance, such as the coatings disclosed in the above mentioned U.S. Pat. Nos. 4,100,309 and 4,642,267.

It is therefore an object of the present invention to provide a new and improved orthodontic elastomeric appliance that is slippery when wetted to enhance the treatment time of a patient.

Another object of the present invention is to provide a polyurethane ligature coated with a hydrophillic polymer blend which renders the ligature slippery when wetted in the mouth of a patient to decrease the coefficient of friction between the metal archwire and the ligature.

In accordance with the present invention, the coating applicable to the elastomeric appliance may comprise a solution of methylene chloride, methyl ethyl ketone and polyvinylpyrrolidone in which the appliances may be dip-coated, and thereafter air-dried and oven-baked. It will be appreciated that the elastomeric appliance of the present invention will be generally referred to as a ligature although it may be a series of ligatures in chain form, as shown in the above referred to U.S. Pat. No. 4,900,250. Further, it will be appreciated that while it is preferable that the ligature herein referred to is molded such as by injection molding, it could be otherwise formed such as by stamping from a sheet of material.

Accordingly, the orthodontic polyurethane ligature of the invention with a polymer coating will substantially reduce the coefficient of friction between the ligature and the archwire to facilitate the movement of brackets along an archwire and decrease the overall treatment time.

Other objects, features and advantages of the invention will be apparent from the following detailed disclosure.

DESCRIPTION OF THE INVENTION

The orthodontic elastomeric appliance such as a ligature according to the invention is preferably formed of polyurethane and preferably molded by suitable injection molding techniques. Thereafter, the formed ligatures are coated with a polymer film that when wetted will exhibit a slippery outer surface.

The preferable coating formulation for the polyurethane ligatures comprises a solution of methylene chloride, methyl ethyl ketone and polyvinylpyrrolidone, in which the ligatures are dip-coated with a soak time of about 2.5 minutes. They are then air-dried for about 10 minutes and oven-baked at about 80° C. for about 20 minutes. The formulation of the coating preferably includes 600 grams of methylene chloride, 400 grams of methyl ethyl ketone, and 10 grams of polyvinylpyrrolidone, having a preferable molecular weight of 360,000. When the ligatures are dry, they look normal and the coating is essentially colorless; but when they are wetted in the mouth, it has been determined in a three-bracket pull test that they produce about a 55 percent reduction in friction force over uncoated ligatures.

While the above coating is generally applicable to elastomeric polyurethane ligatures, it could be applied to any other elastomeric appliances. Further, the above coating is preferably applied by dipping the ligatures in a solution, but it should be appreciated that it could be applied by spraying in order to produce the same coating that would be produced by a 2.5 minute soak time in dipping.

Another form of coating that would produce a hydrophillic film with a low coefficient of friction would be to first dip the ligature in a solution of polyvinylpyrrolidone in a solvent for about one to four minutes, air-drying the ligature to evaporate the solvent, and subjecting the coated ligature to a temperature of about 50° to 100° C. in an oven as a second step. The first step would be to soak the ligature in a solution of polyisocyanate and a solvent and air-drying the ligature before proceeding to step 2. This coating procedure would be in accord with what is disclosed in above referred to U.S. Pat. No. 4,100,309, which is herein incorporated by reference.

Another coating formulation to produce the hydrophillic film on a polyurethane ligature would be a blend such as disclosed in above referred to U.S. Pat. No. 4,642,267, which also is incorporated by reference herein. This coating involves the use of two polymers instead of the coating with a single polymer as in the U.S. Pat. No. 4,100,309.

In view of the foregoing, it is understood that the present invention is to a coated ligature or ligature-like orthodontic appliance and the method of making the appliance which is slippery when wetted to reduce the friction between the ligature and the archwire to facilitate the movement of brackets along an archwire during orthodontic treatment.

It will be understood that modifications and variations may be effected without departing from the scope of the novel concepts of the present invention, but it is understood that this application is to be limited only by the scope of the appended claims.

The invention is hereby claimed as follows:

1. A method of making an orthodontic elastomeric appliance comprising the steps of:

forming an appliance of elastomeric material, and coating the appliance with a hydrophillic polymer blend so that the coefficient of friction of the appliance is substantially decreased when the appliance is wetted.

2. The method of claim 1, wherein the elastomeric material is polyurethane.

3. The method of claim 2, wherein the hydrophillic polymer blend comprises a solution of methylene chloride, methyl ethyl ketone and polyvinylpyrrolidone.

4. The method of claim 3, wherein the methylene chloride is in the amount of 600 grams, the methyl ethyl ketone is 400 grams and the polyvinylpyrrolidone is 10 grams.

5. The method of claim 4, wherein the step of coating includes dip-coating the appliance in the solution with a soak time of about 2.5 minutes.

6. The method of claim 5, which includes the further step of curing the coating on the appliance by air-drying for a period of about 10 minutes and oven-baking at 80 degrees C. for about 20 minutes.

7. The method of claim 4, wherein the polyvinylpyrrolidone has a molecular weight of 360,000.

8. An orthodontic elastomeric appliance having a slippery outer surface when wetted comprising a polyurethane body coated with a hydrophillic polymer blend, whereby said hydrophillic polymer blend decreases the coefficient of friction of the appliance when the appliance is wetted.

9. The elastomeric appliance of claim 8, wherein the appliance is a molded ligature.

10. The polyurethane ligature of claim 9, wherein the hydrophillic polymer blend comprises a solution of methylene chloride, methyl ethyl ketone and polyvinylpyrrolidone.

11. The ligature of claim 10, wherein the coating is cured by air-drying and heat.

12. The ligature of claim 11, wherein the ligature is soaked in the solution for about 2.5 minutes, air-dried for about 10 minutes and baked at 80 degrees C. for about 20 minutes.

13. A method of making an orthodontic appliance of elastomeric material, said method comprising the steps of:

forming an appliance of elastomeric material, and coating the appliance with a polymer film so that the coefficient of friction of the appliance is substantially decreased when the appliance is wetted.

14. The method of claim 13, wherein the material is polyurethane.

15. The method of claim 14, wherein the appliance is a ligature.

16. The method of claim 15, wherein the step of forming is molding.

17. The method of claim 16, wherein the polymer film comprises a solution of methylene chloride, methyl ethyl ketone and polyvinylpyrrolidone.

18. The method of claim 16, wherein the polymer film comprises a solution of polyisocyanate and polyvinylpyrrolidone in a solvent.

19. An orthodontic elastomeric appliance comprising a body of elastomeric material with a polymer coating, whereby the polymer coating decreases the coefficient of friction of the appliance when the appliance is wetted.

* * * * *

UNITED STATES PATENT AND TRADEMARK OFFICE
CERTIFICATE OF CORRECTION

PATENT NO. : 6,203,317 B1
DATED : March 20, 2001
INVENTOR(S) : Thrumal Devanathan It is certified that error appears in the above-identified patent and that said Letters Patent is hereby corrected as shown below:

Change the title to -- ORTHODONTIC ELASTOMERIC APPLIANCE WITH SLIPPERY COATING AND METHOD OF MAKING SAME --

Change the Inventor's name to -- Thrumal Devanathan --

Signed and Sealed this

Twenty-eighth Day of August, 2001

*Attest:*

Nicholas P. Godici

NICHOLAS P. GODICI
*Attesting Officer*  *Acting Director of the United States Patent and Trademark Office*